United States Patent [19]

Morgan

[11] Patent Number: 4,923,471

[45] Date of Patent: May 8, 1990

[54] BONE FRACTURE REDUCTION AND FIXATION DEVICES WITH IDENTITY TAGS

[75] Inventor: Frank H. Morgan, Woodland Hills, Calif.

[73] Assignee: TiMesh, Inc., Calabasas, Calif.

[21] Appl. No.: 422,741

[22] Filed: Oct. 17, 1989

[51] Int. Cl.⁵ ............................................. A61F 2/28
[52] U.S. Cl. ...................................... 623/16; 606/60; 606/69
[58] Field of Search ................ 623/16, 17, 18, 19, 623/20, 21, 22; 606/60, 61, 69, 70, 71; 128/69

[56] References Cited

U.S. PATENT DOCUMENTS

| D. 288,238 | 2/1987 | Homsy et al. | 623/16 |
| 3,488,779 | 1/1970 | Christensen | 623/16 |
| 4,769,040 | 9/1988 | Wevers | 623/20 |

FOREIGN PATENT DOCUMENTS 468123  3/1974  Australia ................ 128/69

Primary Examiner—Randall L. Green
Assistant Examiner—David H. Willse
Attorney, Agent, or Firm—Philip D. Junkins

[57] ABSTRACT

The present invention relates to a bone fracture reduction device for the internal fixation and immobilization of bone fragments. The device is comprised of a thin malleable bone affixation plate, formed of a biocompatible metallic material with at least two spaced openings extending therethrough each for receiving a bone screw, with a thin bone plate identification tag formed as an integral extension of the bone affixation plate. The identification tag bears at least the name of the plate manufacturer, the manufacturer's product number, and the manufacture's production lot number for the bone affixation plate to provide full traceability of the device, and the identification tag provides the surgeon using the bone plate with means for handling and manipulating the plate during its affixation to bone fragments at a fracture site and after plate affixation the tag is severable from the plate for archiving.

7 Claims, 1 Drawing Sheet

U.S. Patent    May 8, 1990    4,923,471
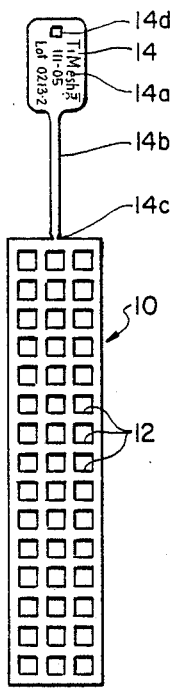
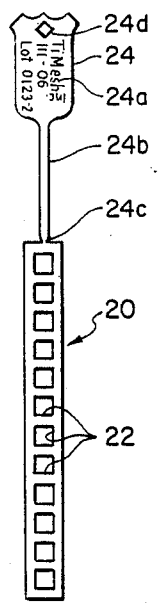
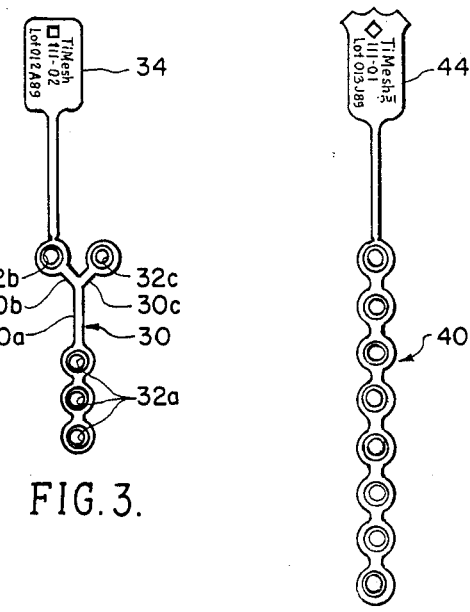
FIG. 1.   FIG. 2.   FIG. 3.   FIG. 4.
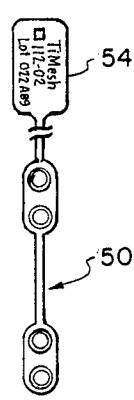
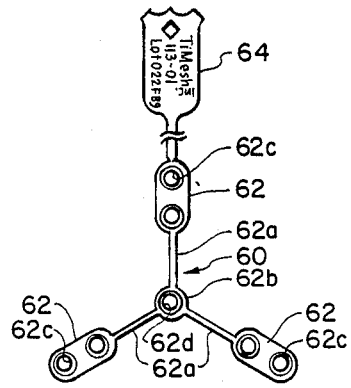
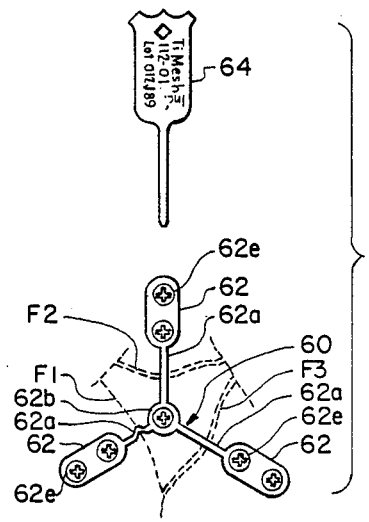
FIG. 5.   FIG. 6.   FIG. 6a.
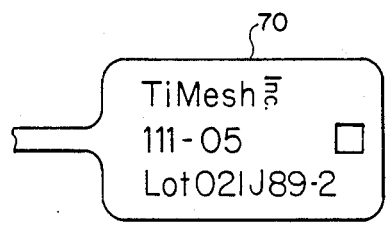
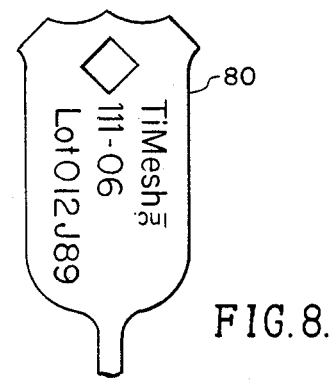
FIG. 7.   FIG. 8.

BONE FRACTURE REDUCTION AND FIXATION DEVICES WITH IDENTITY TAGS

BACKGROUND OF THE INVENTION

A bone fracture is a traumatic disruption of the continuity of a bone. If there is relative motion of the bone fragments at the fracture site, irritation of the surrounding tissues and heavy pain ensue and the time of fracture healing is usually extended. Proper rejoining of bone fragments is thus dependent upon immobilization of the fracture site. Classically, bone fragment reduction (bone fragments properly aligned and abutted along the fracture line or lines) and immobilization for limb bones has been accomplished by external limb casts. Such casts must be worn for long periods of time, are heavy and unbalancing to the body skeletal structure and muscular system, inhibit bone vascularity (promotes fast and effective bone healing), and may result in bone resorption because of the total absence of tensile and compressive functional loading throughout the fractured bone structure. Fractures in bones other than the arms and legs are more difficult to immobilize and the use of exterior casts may not be possible, particularly in the facial areas.

Over the past twenty years the use of stabilization and compression plate techniques for internal fixation of fractures has been developed and widely applied. With internal fixation, by means of bone screws and plates particularly plates made of biocompatible metals and metal alloys such as titanium, stainless steel and cobalt-chromium), immediate and absolute immobilization is achieved through interfragmentary stabilization and compression. Other materials and devices such as wires, intramedullary nails or externally fixed pins are used mainly to reduced bone fracture mobility and improve the position of the fracture segments. The aim of internal bone fracture fixation is to allow early, pain-free movement and use of the injured limb, mandible, etc., thus avoiding the consequences of long lasting immobilization, i.e., bone fracture disease, bone resorption, etc.

With internal bone fixation it is important that the application of the stabilization or compression plate or fracture reduction device result in relative immobility of the bone fragments and tight closure of the fracture interface or fracture interfaces. Without such immobility and tight closure, changing tension and compression loads tend to produce relative motion between the fracture fragments with resultant undesirable fragment shortening due to bone resorption. Through the proper use of a bio-compatible metallic fracture reduction device (a surgically applied implant), static forces applied as interfragmentary compression by the device prevent relative motion between the fracture interfacing surfaces. Thus, compressive pre-loading of the bone fragments (through the stabilization or compression device) prevents relative motion at the fracture site in spite of functional use of the limb, mandible, etc., without external immobilization or splinting. With mechanical stimuli (forces and motion) permitted via the internal bone fixation techniques, rapid and healthy healing of the fracture is promoted and bone vascularity is maintained and restored. Vascularity of bone is interrupted by the fracture trauma and by surgical intervention (application of the bone fixation device or devices) but revascularization is restored and enhanced by the rigid immobilization of the bone fragments or fracture interfaces through internal fixation techniques.

During the early application of stabilization and compression device techniques, the devices were meant to be merely fixed to the bone fragments of the fracture for alignment purposes. Later, the value of interfragmentary compression, through devices and plates applied under tension, was recognized. A number of internal fixation devices have been developed with built-in compression devices—devices for tensioning the device or plate to create interfragmentary compression. Some of such systems have required that the plate-tensioning device remain implanted with the plate. Other systems have been designed with removable plate-tensioning apparatus.

Further developments in compression plate designs and attachment screws (also formed of bio-compatible metals and metal alloys—particularly titanium) have related to screw head and screw hole geometry, i.e., conical geometry of the screw shoulder and oval screw holes in the compression plate for promoting bone fragment compression during screw application. Attempts to obtain optimal stability of fixation have most recently resulted in the use congruent fitment between screw head and screw hole including both conical countersunk screw holes and hemicylindrical screw holes.

Numerous problems remain in the application of the various compression plate systems that are commercially available for internal bone fixation. Some systems require great care in the installation of bone screws so that their orientation is always perpendicular to the plate. When contouring a plate to fit a curved bone surface, circularly fitting screw holes may become distorted and cause high friction against screw rotation or may completely inhibit a screw from entering the screw hole. Buckling or kinking of bone fragments at the fracture line may occur as a result of improper tensioning at the end of the compression plate during plate application.

In the last 10-15 years titanium mesh sheets and strips have gained wide-spread use in reconstructive, orthognathic and trauma surgery with excellent clinical results and implant survival rates. The malleability of such sheets and strips allows quick and easy bending for adaption to bone contours. In more recent years small bone plates in numerous configurations have come into high use in maxillofacial reconstructive surgery with such plates being deformable and contourable for fitment to virtually every fracture or osteotomy no matter how complex or how irregular the surgical site. Thus, contourable bone plates of "Y", "T", "L" and "I" shape configurations, and of more complex geometrical shapes, are available in a variety of thicknesses and with a selection of degrees of malleability.

Many of the implantable titanium mesh sheets and strips, and titanium plates, as described above, are relatively small (25-40 mm. in their major dimension) and difficult to maneuver into, and hold at, the appropriate fracture site location during affixation to bone fragments, particularly in maxillofacial areas which have experienced severe trauma. It is also of concern to the entire medical community dealing with implantable devices and products that material biocompatibility, durability and structural integrity, and sterility be assured in compliance with increasing interest in and control by the Food and Drug Administration in the United States.

It is a principal object of the present invention to provide unique implantable bone fracture reduction devices of relatively small but effective structure which can be easily manipulated and applied in surgical procedures involving the internal fixation of fractures.

It is a further object of the invention to provide perforated metallic sheets and strip and metallic bone plates, for use as implantable devices in the internal reduction and fixation of bone fractures, which may be easily and rapidly installed over complex or irregular surgical sites, and which have associated therewith a removable tag portion for handling of the devices during their installation and for thereafter providing identifying historical information respecting the type and structural integrity of such devices.

It is a still further object of the invention to provide relatively small implantable bone fracture internal fixation devices which may be easily held and manipulated by removable identifying implant tag portions which provide historical information respecting the type and manufacturing and structural integrity of such devices.

It is yet another object of the invention to provide small implantable metallic bone fracture internal fixation devices which may be easily held and manipulated by integral, removable identifying implant tag portions which are metallurgically identical to the implantable devices and which comprise a "witness sample" of the devices for archiving and subsequent retrieving to yield historical information respecting the product type, material specifications, manufacturing procedures and quality controls applicable to such devices.

Other objects and advantages of the invention will be apparent from the following summary and detailed description of the bone fracture reduction and fixation devices of the invention taken together with the accompanying drawing figures.

SUMMARY OF THE INVENTION

The present invention relates to improved bone fracture reduction devices for use in the internal fixation of bone fractures and the immobilization of the fracture fragments. The bone fracture reduction devices of the invention, formed of biocompatible metal and metal alloys such as titanium, stainless steel and cobalt-chromium, have a size, structure and configuration dependent upon the size, arrangement and location of the bone fragments requiring internal fixation and immobilization. The bone fracture reduction devices of the invention are relatively small (many having a major dimension of about 25 mm. to about 40 mm.) and are paticularly applicable to fractures of the human skull or cranium.

The metallic fracture reduction devices of the invention are thin perforated mesh sheets and strips and thin plates (containing two or more screw holes) of "Y", "T", "L" and "I" shape configuration or of more complex geometrical shapes including deformable leg portions. The bone fracture reduction devices are held in place by biocompatible (like metal or alloy) bone screws set into abutting bone fragments with the mesh or plate leg portions extending across the fracture lines between such fragments. Before affixation the reduction devices (of varying degrees of malleability) may be contoured to comply with the bone irregularities and topography presented at the fracture site. After partial or full affixation the leg portions of the devices may be bent or kinked to reduce the effective lengths thereof to create tension forces through the leg portions thereby applying compression force or loading to the fracture interfaces of the bone fragments with the result that the fracture of fractures are reduced and immobilized.

In accordance with the present invention, each implantable metallic fracture reduction devices (mesh sheet or strip, or geometrically configured bone plate) bears as an integral part thereof a depending or projecting product identification tag which may be utilized, during at least the initial stages of device affixation, to hold and manipulate the device. After the affixation of the fracture reduction device to the bone fragments, the metallurgically identical identification tag portion thereof may be easily removed from the device (cut at the point of its joinder to the device) and retained for further reference as to the manufacturer's identity, product number and production lot number. Such identification information provides the reconstructive surgeon utilizing the implantable device with full traceability of the product and product type to the manufacturer and the material specifications, manufacturing procedures and quality controls applicable to the device.

BRIEF DESCRIPTION OF THE DRAWING FIGURES

FIG. 1 is a top plan view of a malleable, perforated, metallic, mesh-type bone fracture reduction plate or sheet in accordance with the present invention showing one form of an integral, severable implant product identification tag which provides ease of plate handling and manipulation during affixation thereof to bone fragments at a fracture site;

FIG. 2 is a top plan view of a perforated metallic bone fracture reduction strip showing another form of an associated product identification tag in accordance with the invention;

FIG. 3 is a top plan view of a malleable metallic "Y" shaped bone plate with appropriate bone screw holes for mounting the plate to bone fragments, such plate including deformable leg portions and a severable implant product identification tag;

FIG. 4 is a top plan view of a deformable metallic bone plate strip with appropririate bone mounting holes and a severable implant holding and manipulating product identification tag;

FIG. 5 is a top plan view of another deformable metallic bone plate strip with an associated and severable product identification tag;

FIG. 6 is a top plan view of another "Y" shaped metallic bone plate with deformable leg or arm portions with outboard screw hole portions and with an associated and severable product holding and identification tag;

FIG. 6a is a top plan view of the "Y" shaped bone plate of FIG. 6 in affixed placement position with respect to a complex bone fracture, with one of the legs of the plate kinked to close the fracture line straddled by such leg, and with the associated product holding and identification tag separated from the plate;

FIG. 7 is an enlarged top plan view of one form of a product identification tag associated with the bone reduction devices of the invention showing a manufacturer's name, product catalog number and manufacturing lot number; and FIG. 8 is an enlarged top plan view of another stylized form of a product identification tag associated with the bone reduction devices of the invention.

It should be noted that no side or edge view has been shown of any of the bone reduction devices illustrated in FIGS. 1 through 6a, or of either of the product identification tag forms shown in FIGS. 7 and 8, since such devices and tags are all of flat metallic structure having a thickness in the range of about 0.6 mm. to about 1.2 mm.

DETAILED DESCRIPTION OF THE INVENTION

Referring to FIG. 1 of the drawing sheet, there is illustrated in a top plan view a bone fracture reduction device 10 of the invention in the form of a malleable, perforated, metallic, mesh-type sheet which provides the user with a matrix of holes or perforated openings 12 through which bone screws may be applied to bone fragments at a fracture site. Affixed to, and a part of, the mesh-type reduction device is a severable implant product identification tag 14 which provides the surgeon utilizing the device with a handle for holding and manipulating such device during its placement and affixation to bone fragments at the fracture site via multiplicity of biocompatible bone screws (not shown).

The ID tag 14 bears manufacturer name identification, product catalog number designation and manufacturing lot number designation 14a and is attached to the bone fracture reduction device (mesh sheet) 10 via an integral tag leg or stem portion 14b. At the point of joinder of the tag leg portion 14b to the bone fracture reduction device 10 there is provided a reduced neck area 14c which makes the ID tag 14 easily severable from the device 10 either by cutting of the metal at the neck area or by twisting flexure of the ID tag 14 to break it away from the device 10. After implantation of the bone fracture reduction device 10, with its affixation to bone fragments at a fracture site, the severed ID tag 14 (with its leg or stem portion 14b) may be placed in the patients surgery file for subsequent identifying and or billing use with respect to the implant product. For retainment purposes the ID tag 14 is therefore provided with a perforation or hole 14d whereby the tag may be clipped, stapled or otherwise affixed to the patient file.

In FIG. 2 there is shown, in a top plan view, another bone fracture reduction device 20 of the invention in the form of a malleable, perforated, metallic, mesh-type strip which provides the user-surgeon with a straight course of holes or perforations 22 through which bone screws may be applied to affix the implantable device for fracture reduction at the fracture site. Affixed to, and a part of, the strip 20 is a severable implant product identification tag 24, of alternative design, which is available to the surgeon for holding and manipulating such strip during its placement and affixation to bone fragments at the fracture site via bone screws. As in the case of the ID tag 14 shown in FIG. 1, the ID tag 24 bears the manufacturer's name, product catalog number and manufacturing lot number designations 24a and is attached to the bone fracture reduction device (mesh strip) 20 via an integral tag leg portion 24b. The ID tag or "witness sample" 24 of the implantable strip 20, as illustrated in FIG. 2, is of shield configuration and the tag (with its leg portion 24b) is severable from the implantable device 20 at the reduced neck area 24c proximate the point whereat the tag leg portion 24b attaches to the device 20. As with the ID tag 14 of FIG. 1, the ID tag 24 of FIG. 2 is provided with a perforation or hole 24d whereby the tag may be clipped, stapled or otherwise affixed to the patient file.

In FIG. 3 of the drawing sheet there is illustrated in a top plan view a bone fracture reduction device 30 of the invention in the form of a malleable (deformable), metallic plate of "Y" shape. The plate 30 includes leg portions 30a, 30b and 30c each provided with mounting holes 32a, 32b and 32c, respectively, for receiving biocompatible bone screws (not shown) during the mounting of the plate 30 to bone fragments at a fracture site. Affixed to, and a part of, the "Y" shaped bone plate 30 is a severable implant product identification tag 34 of the type shown in FIG. 1 and described hereinbefore.

In FIGS. 4, 5 and 6 there are illustrated additional malleable (deformable), metallic bone plates 40, 50 and 60, respectively, of various designs with each such plates provided, in accordance with the invention, with associated severable implant product identification tags 44, 54, and 64, respectively. Each of these bone plates is provided with an appropriate number of screw holes for mounting of such plates to bone fragments at a fracture site.

In FIG. 6a the "Y" shaped bone fracture reduction plate 60 of FIG. 6 is shown mounted to bone fragments at a fracture site involving a complex system of fracture lines F1, F2, and F3 illustrated by dashed line representations. The bone plate 60 includes three like outboard bone affixation portions 62, each interconnected by a relatively narrow leg section 62a to an intermediate or hub bone affixation portion 62b. The outboard bone affixation portions 62 of the plate 60 each contain two counter-sunk screw holes (see FIG. 6 for screw holes 62c) and the hub porton 62b (as shown in FIG. 6) contains a single counter-sunk screw hole 62d. The bone plate 60 is mounted to the fracture site bone fragments via bone screws 62e (see FIG. 6a). To close an open fracture line (after appropriate affixation of the "Y" shaped plate 60 to adjacent bone fragments) the plate legs 62a may be kinked, to a relatively more or less extent. As shown in FIG. 6a the fracture line F1 has been closed by kinking of the plate leg 62a which spans such fracture line. The other fracture lines F2 and F3 (as shown) remain open with the spanning plate leg 62a in each case still in its original non-deformed shape at full length. As shown in FIG. 6a, the ID tag 64, originally an integral part of the plate 60, has been severed from the plate.

Kinking of the interconnecting plate legs of bone plates of the type shown in FIGS. 5 and 6 (after such plates have been secured to the bone fragments presenting open fracture lines) may be accomplished by the use of "Aderer" type pliers commonly used by orthodontists for kinking wires connecting orthodontic bands to increase the tension forces applied by such wires to such bands. This type of plier has two prongs on one side and one prong on the opposing side of the plier jaws. Kinking deformation of the leg sections of bone plates may also be accomplished by "needle nose" type pliers of well-known design.

The preferred material of construction of the metallic mesh-type sheets and strips forming bone fracture reduction devices in accordance with the invention, and of bone plates of the type described hereinbefore, is commercially pure titanium with a yield strength in the range of 30,000 to 40,000 psi. Bone screws utilized to accomplish internal fracture fixation in accordance with the invention should also preferably be fabricated from commercially pure titanium. Also, the armamentarium (tools) utilized should have working parts and surfaces of the same biocompatible metal or metal alloy so as to avoid foreign metal contamination of the bone fixation devices.

In FIGS. 7 and 8 of the drawing sheet there is shown enlarged views of the product identification tags illustrated in FIGS. 1-6. Thus, in FIG. 7 the ID tag 70 is an enlarged showing of the tag portion of the internal bone fixation devices of FIGS. 1, 3 and 5 and in FIG. 8 the ID tag 80 is an enlarged showing of the tag portion of the internal bone fixation devices of FIGS. 2, 4 and 6. As previously mentioned, the fixation devices illustrated in FIGS. 3–6 and 6a are of relatively small size having a major dimension of about 25 mm. to about 40 mm. Also, the bone fixation devices of all figures are (in their "as supplied" form) of flat structure having a thickness in the range of about 0.6 mm. to about 1.2 mm.

It is to be understood that further alternative configurations of implantable bone fracture reduction devices, in accordance with the invention, have been fabricated. Also, it should be apparent that numerous other shapes of the identification tag portion of the implantable devices of the invention can be formed as integral parts thereof. After the affixation of a fracture reduction device to bone fragments at a fracture site, the identification tag portion thereof may be easily removed from the device and retained for further reference as to the manufacturer's identity, product number and production lot number. Such identification information provides the reconstructive surgeon and associated medical team administrative authorities with full traceability of the product to the manufacturer and the material specifications, manufacturing procedures and quality controls applicable to the implantable device.

While the invention has been described in connection with particular structural embodiments of bone fracture reduction devices, many modifications of the invention will be apparent to those skilled in the art. Accordingly, such modifications are to be included within the spirit and scope of the invention as defined by the following claims.

What is claimed is:

1. An implantable bone fracture reduction device for the internal fixation and immobilization of bone fragments at a bone fracture site comprising:
   (a) a thin malleable bone affixation plate formed of a biocompatible metallic material, said plate having at least two spaced openings extending therethrough each for receiving a bone screw to be driven into bone fragments at a fracture site to affix said plate to said bone fragments; and
   (b) a thin bone plate identification tag formed as an integral extension of said bone plate, said identification tag bearing at least the name of the plate manufacturer, the manufacturer's product number, and the manufacturer's production lot number for said plate to provide full traceability of the device with respect to material specifications, manufacturing procedures and quality controls, and said identification tag providing means for handling and manipulating said bone plate during its affixation to bone fragments at a fracture site and being severable from said bone plate for archiving.

2. An implantable bone fracture reduction device for the internal fixation and immobilization of bone fragments at a bone fracture site as claimed in claim 1 wherein said thin malleable bone affixation plate comprises a generally rectangular perforated mesh-type structure fabricated of a biocompatible metal or metallic alloy selected from the group consisting of titanium, titanium alloys, cobalt-chromium alloys and stainless steels, said severable bone plte identification tag extending from one end of said mesh-type structure.

3. An implantable bone fracture reduction device for the internal fixation and immobilization of bone fragments at a bone fracture site as claimed in claim 1 wherein said thin malleable bone affixation plate includes two plate sections interconnected by a relatively narrow deformable leg section with at least two screw holes extending through each plate section, the screw holes of each plate section being in general alignment with the long axis of said leg section, said severble bone plate identification tag extending from one of said plate sections.

4. An implantable bone fracture reduction device for the internal fixation and immobilization of bone fragments at a bone fracture site as claimed in claim 1 wherein said thin malleable bone affixation plate includes two terminal plate sections with at least two screw holes extending therethrough, an intermediate plate section having at least one screw hole extending therethrough, and two relatively narrow deformable leg sections with each of said leg sections interconnecting one of said terminal plate sections to said intermediate plate section, said severable bone plate identification tag extending from one of said terminal plate sections.

5. An implantable bone fracture reduction device for the internal fixation and immobilization of bone fragments at a bone fracture site as claimed in claim 1 wherein said thin malleable bone affixation plate includes three or more terminal plate sections with at least two screw holes extending therethrough, a central hub-type plate section having a single screw hole extending therethrough, and a relatively narrow deformable leg section interconnecting each of said terminal sections with said central plate section, said severable bone plate identification tag extending from one of said terminal plate sections.

6. An implantable bone fracture reduction device for the internal fixation and immobilization of bone fragments at a bone fracture site as claimed in claim 1 wherein said thin malleable bone affixation plate includes three or more like bone plate sections each with at least one screw hole extending therethrough, each of said plate sections interconnected by relatively narrow deformable leg sections of equal or unequal length to two adjacent like plate sections whereby said bone plate takes on the form of a closed multiple sided geometrical plane figure, said severable bone plate identification tag extending from one of said plate sections.

7. An implantable bone fracture reduction device for the internal fixation and immobilization of bone fragments at a bone fracture site as claimed in claims 3, 4, 5, 5, or 6 wherein said thin malleable bone affixation plate is fabricated of a biocompatible metal or metallic alloy selected from the group consisting of titanium, titanium alloys, cobalt-chromium alloys and stainless steels.

* * * * *